US008833306B2

(12) United States Patent
Lugo González et al.

(10) Patent No.: US 8,833,306 B2
(45) Date of Patent: Sep. 16, 2014

(54) PACAP FOR AQUATIC ORGANISM CULTURE

(75) Inventors: Juana Maria Lugo González, La Habana (CU); Mario Pablo Estrada Garcia, Ciudad de la Habana (CU); Alina Rodriguez Mallon, Ciudad de la Habana (CU); Yamila Carpio González, Ciudad de la Habana (CU); Antonio Morales Rojas, Ciudad de la Habana (CU); Osmany Rodrigo González De Sosa, Ciudad de la Habana (CU); Reynold Morales Fernández, Ciudad de la Habana (CU); Fidel Francisco Herrera Miyares, Ciudad de la Habana (CU)

(73) Assignee: Centro de Ingenieria Genetica Y Biotecnologia, Ciudad de la Habana (CU)

( * ) Notice: Subject to any disclaimer, the term of this patent is extended or adjusted under 35 U.S.C. 154(b) by 797 days.

(21) Appl. No.: 12/094,339

(22) PCT Filed: Nov. 20, 2006

(86) PCT No.: PCT/CU2006/000013
§ 371 (c)(1),
(2), (4) Date: Sep. 26, 2008

(87) PCT Pub. No.: WO2007/059714
PCT Pub. Date: May 31, 2007

(65) Prior Publication Data
US 2009/0176703 A1    Jul. 9, 2009

(30) Foreign Application Priority Data

Nov. 22, 2005    (CU) ..................................... 0231/05

(51) Int. Cl.
*A61K 38/18*    (2006.01)
*A01K 61/00*    (2006.01)
*A01K 61/02*    (2006.01)

(52) U.S. Cl.
USPC ........... 119/204; 119/210; 119/215; 119/230; 514/11.3; 530/399

(58) Field of Classification Search
None
See application file for complete search history.

(56) References Cited

U.S. PATENT DOCUMENTS 5,695,954 A * 12/1997 Sherwood et al. ........... 435/69.1
2003/0084469 A1    5/2003    Chang et al.

FOREIGN PATENT DOCUMENTS

EP    0387457 A1    9/1990
EP    1447181 A1    11/2004
WO    9426897 A    11/1994

OTHER PUBLICATIONS

Garrett et al., Emerging Infectious Diseases, 1997; 3: 453-457.*
McRory et al., Mol Cell Endocrinol. 1995; 108: 169-77.*
Matsuda et al., Peptides, 2005; 26: 1611-1616.*
Nejigaki et al., Journal of Experimental Zoology, 2006; 305A: 161-EOA; abstract #P4.18.*
Carpio et al., Fish & Shellfish Immunology, 2008; 25: 439-445.*
Wong et al., Endocrinol. 1998; 139: 3465-3479.*
Lugo et al., Journal of Endocrinol. 2008; 197: 583-597.*
Maruyama et al., Peptides, 2006; 27: 1820-1826.*
Acosta et al., Biotechnol Lett. 2007; 29: 1671-1676.*
Clara Pena et al., "Synthesis and Properties of Human Growth Hormone Fragments," Int. J. Peptide Protein Res. 18, 1981, 289-296.
Elio F. De Palo et al., "Growth Hormone Isoforms and Segments/Fragments: Molecular structure and laboratory measurement," Clinica Chimica Acta 364, 2006, 67-76.
Matsuda, K. et al., "Anorexigenic action of pituitary adenylate cyclase-activating polypeptide (PACAP) in the goldfish: feeding-induced changes in the expression of mRNAs for PACAP and its receptors in the brain, and locomotor response to central injection," Neurosci. Lett., vol. 386, Sep. 2005, pp. 9-13.

* cited by examiner

*Primary Examiner* — Christina Borgeest
(74) *Attorney, Agent, or Firm* — Hoffmann & Baron LLP

(57) ABSTRACT

The present invention is related to the use of variants of the Pituitary Adenylate Cyclase-Activating Polypeptide (PACAP) to stimulate the growth and to improve the immunological system of aquatic organisms. The variants of the peptide were provided by immersion, injection or as a food additive.

21 Claims, 5 Drawing Sheets

SEQUENCE LISTING

<160> NUMBER OF SEQ ID NOS: 14

<210> SEQ ID NO 1
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 1
gcagccatgg ccaaatctag tagagctac                                    29

<210> SEQ ID NO 2
<211> LENGTH: 31
<212> TYPE: DNA
<213> ORGANISM: Artificial Sequence
<220> FEATURE:
<223> OTHER INFORMATION: Synthetic nucleotide sequence

<400> SEQUENCE: 2
ggaattcctt taatggcttg acttcgtaca t                                 31

<210> SEQ ID NO 3
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 3
catccatatg cactcggacg gcattttcac gg                                32

<210> SEQ ID NO 4
<211> LENGTH: 38
<212> TYPE: DNA
<213> ORGANISM: Artificial Sequence
<220> FEATURE:
<223> OTHER INFORMATION: Synthetic nucleotide sequence

<400> SEQUENCE: 4
cgggatcctt atttgtttct aaacctctgt ctgtacct        38

<210> SEQ ID NO 5
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 5
cactcggacg gcattttcac gg        22

<210> SEQ ID NO 6
<211> LENGTH: 31
<212> TYPE: DNA
<213> ORGANISM: Artificial Sequence
<220> FEATURE:
<223> OTHER INFORMATION: Synthetic nucleotide sequence

<400> SEQUENCE: 6
actagtttat tgtttctaa acctctgtct g        31

<210> SEQ ID NO 7
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 7
ccatgggaca ctcggacggc attttcacgg        30

<210> SEQ ID NO 8
<211> LENGTH: 727
<212> TYPE: DNA
<213> ORGANISM: Artificial Sequence
<220> FEATURE:
<223> OTHER INFORMATION: Synthetic nucleotide sequence

<400> SEQUENCE: 8
atggccaaat ctagtagagc tactttggct ctgctcatct acgggatctt aatgcgctac        60
acgcccaatg cacacccatc ggaatgggct tccccaatat gaggctagaa aacgacgtgt       120
tcggggacga gggaaactcg ttaagtgagc tgtcctacga gccggacacg atgagcgcgc       180
gcagtgctcc agccctccct gaagacgcat acacactgta ctacccgccc gagagaagag       240
ccgaaacgca tgcagacgga ttgttagata gagccttgag ggacatcctg gttcagttat       300
cagcccgaaa atatctgcat tctctgacgg cagttcgcgt aggtgaggaa gaagaggatg       360
aagaggactc ggagccactg tcgaagcgcc actcggacgg cattttcacg gacagctaca       420
gccgctaccg gaaacaaatg gccgtaaaaa ataccttgc agcagtgctg ggaagaaggt       480
acagacagag gtttagaaac aaaggacgcc gctttgctta tttgtagcgg ataggaagaa       540
aaggaaagaa agaaaaaaac gcgagagaga gagagagaga gagaaataga gcaactgccc       600
tcccttgtgt ccattcaatc atacagtcag aagtctggta tctaacttaa cactgagcag       660
tcagtcggtg gatctcgcct gtgttctttt aaacatgtat tttatgtacg aagtcaagcc       720
attaaag                                                                 727

<210> SEQ ID NO 9
<211> LENGTH: 86
<212> TYPE: PRT
<213> ORGANISM: Clarias gariepinus

<400> SEQUENCE: 9

Met His Ala Asp Gly Leu Leu Asp Arg Ala Leu Arg Asp Ile Leu Val
1               5                   10                  15

Gln Leu Ser Ala Arg Lys Tyr Leu His Ser Leu Thr Ala Val Arg Val
            20                  25                  30

Gly Glu Glu Glu Asp Glu Glu Asp Ser Glu Pro Leu Ser Lys Arg
        35                  40                  45

His Ser Asp Gly Ile Phe Thr Asp Ser Tyr Ser Arg Tyr Arg Lys Gln
    50                  55                  60

Met Ala Val Lys Lys Tyr Leu Ala Ala Val Leu Gly Arg Arg Tyr Arg
65                  70                  75                  80

Gln Arg Phe Arg Asn Lys
                85

<210> SEQ ID NO 10
<211> LENGTH: 114
<212> TYPE: DNA
<213> ORGANISM: Clarias gariepinus

<400> SEQUENCE: 10
cactcggacg gcattttcac ggacagctac agccgctacc ggaaacaaat ggccgtaaaa      60
aaataccttg cagcagtgct gggaagaagg tacagacaga ggtttagaaa caaa           114

<210> SEQ ID NO 11
<211> LENGTH: 114
<212> TYPE: DNA
<213> ORGANISM: Tilapia nilotica

<400> SEQUENCE: 11
cactcggacg gcattttcac ggacagctac agccgctacc ggaaacaaat ggcagtaaaa      60
aagtatcttg cagcagtgct gggaagaagg tacagacaga ggtttagaaa caaa           114

<210> SEQ ID NO 12
<211> LENGTH: 40
<212> TYPE: PRT
<213> ORGANISM: Clarias gariepinus

<400> SEQUENCE: 12

Met Gly His Ser Asp Gly Ile Phe Thr Asp Ser Tyr Ser Arg Tyr Arg
1               5                   10                  15

Lys Gln Met Ala Val Lys Lys Tyr Leu Ala Ala Val Leu Gly Arg Arg
            20                  25                  30

Tyr Arg Gln Arg Phe Arg Asn Lys
        35                  40

<210> SEQ ID NO 13
<211> LENGTH: 39
<212> TYPE: PRT
<213> ORGANISM: Clarias gariepinus

```
<400> SEQUENCE: 13

Met His Ser Asp Gly Ile Phe Thr Asp Ser Tyr Ser Arg Tyr Arg Lys
1               5                  10                  15

Gln Met Ala Val Lys Lys Tyr Leu Ala Ala Val Leu Gly Arg Arg Tyr
                20              25                  30

Arg Gln Arg Phe Arg Asn Lys
        35

<210> SEQ ID NO 14
<211> LENGTH: 38
<212> TYPE: PRT
<213> ORGANISM: Clarias gariepinus

<400> SEQUENCE: 14

His Ser Asp Gly Ile Phe Thr Asp Ser Tyr Ser Arg Tyr Arg Lys Gln
1               5                  10                  15

Met Ala Val Lys Lys Tyr Leu Ala Ala Val Leu Gly Arg Arg Tyr Arg
                20              25                  30

Gln Arg Phe Arg Asn Lys
        35
```

PACAP FOR AQUATIC ORGANISM CULTURE

This application is the U.S. National Phase of, and Applicants claim priority from, International Application Number PCT/CU2006/000013 filed 20 Nov. 2006 and Cuban Application bearing Serial No. CU2005-0231 filed 22 Nov. 2005, which are incorporated herein by reference.

TECHNICAL FIELD

The present invention is related to the field of the farming biotechnology, specifically with the use of the Pituitary Adenylate Cyclase-Activating Polypeptide in the aquatic organism culture. The application of the peptide to aquatic organisms by immersion, injection or as a feed additive, produces an increase in the appetite of these organisms, a greater rate of growth and survival, a superior immune activity and an increase of the prolactin liberation.

INCORPORATION OF SEQUENCE LISTING

Incorporated herein by reference in its entirety is the Sequence Listing for the application. The Sequence Listing is disclosed on a computer-readable ASCII text file titled, "sequence.txt", created on Jan. 26, 2009. The sequence.txt file is 6 kb in size.

PREVIOUS ART

The Pituitary Adenylate Cyclase-Activating Polypeptide (PACAP) was isolated for the first time in 1989 from bovine hypothalamus and was demonstrated that its capacity to stimulate the growth hormone secretion through the adenylate cyclase enzyme activation. (Miyata and col. (1989) Isolation of a novel 38 residue hypothalamic polypeptide which stimulates adenylate cyclase in pituitary cells. *Biochem. Biophys. Res. Commun.* 164:567-574). PACAP belongs to the peptide family that includes the secretin, glucagon and the intestinal vasoactive peptide (Arimura and Shioda (1995) Pituitary adenylate cyclase-activating polypeptide (PACAP) and its receptors: Neuroendocrine and endocrine interaction. *Front. Neuroendocrinol.* 16:53-88). In mammals, the precursors of the PACAP and the Growth Hormone Releasing Hormone (GHRH) are codified by two different genes (Hosoya and col. (1992) Structure of the human pituitary adenylate cyclase-activating polypeptide (PACAP) gen. *Biochim. Biophys. Acta.* 1129:199-206). In the all submammalian species studied to date (birds, reptiles and fish), GHRH and PACAP peptides are codified by the same gene and are contained in the same precursor (Montero and col. (2000) Molecular evolution of the growth hormone-releasing hormone/pituitary adenylate cyclase-activating polypeptide gene family. Functional implication in the regulation of growth hormone secretion. *Journal of Molec. Endocrinol.* 25:157-168). The PACAP gene is expressed fundamentally in: central and peripheral nervous system, the eyes innerving nervous fibers, the respiratory tract, the salivary glands, the gastrointestinal tract, reproductive system organs, the pancreas and the urinary tract. Also it is synthesized in the adrenal glands, in the gonad and in the immune cells (Sherwood and col. (2000) The origin and function of the Pituitary Adenylate Cyclase-Activating Polypeptide (PACAP)/Glucagon Superfamily. *Endocrine Review* 21:619-670). PACAP displays different biological functions, which is consistent with its diverse distribution in different tissue and with its hypophysiotropic, neurotransmitter, neuromodulate and vasoregulate activity. (Chatterjee and col. (1997) Genomic organization of the rat pituitary adenylate cyclase-activating polypeptide receptor gene. Alternative splicing within the 59-untranslated region. *J. Biol. Chem.* 272:12122-12131).

It is involved in the regulation of the cellular division, differentiation and death (Sherwood and col. (2000) The origin y function of the Pituitary Adenylate Cyclase-Activating Polypeptide (PACAP)/Glucagon Superfamily. *Endocrine Review* 21:619-670).

PACAP stimulates the growth hormone (GH) liberation. The peptide effect in the GH liberation has been demonstrated in vitro in several species of mammals, birds, amphibians (Hu and col. (2000) Characterization and messenger ribonucleic acid distribution of a cloned pituitary adenylate cyclase-activating polypeptide type I receptor in the frog *Xenopus laevis* brain. *Endocrinol.* 141:657-665) and fish (Anderson L. L. and col. (2004) Growth Hormone Secretion: Molecular and Cellular Mechanisms and In Vivo Approaches. *Society for Experim. Biol. and Med.* 229:291-302). There are few studies about the effect of PACAP in the GH secretion and liberation, in vivo. To date it is known that this peptide increases in vivo the levels of the GH in rat plasma (Jarr and col. (1992) Contrasting effects of pituitary adenylate cyclase activating polypeptide (PACAP) on in vivo and in vitro prolactin and growth hormone release in male rats. *Life Sci.* 51:823-830) and in bovine plasma (Radcliff and col. (2001) Pituitary adenylate cyclase-activating polypeptide induces secretion of growth hormone in cattle. *Domestic. Animal. Endocrinol.* 21:187-196). Whereas in ewes (Sawangjaroen and Curlewis (1994) Effects of pituitary adenylate cyclaseactivating polypeptide (PACAP) and vasoactive intestinal polypeptide (VIP) on prolactin, luteinizing hormone and growth hormone secretion in the ewe. *J. Neuroendocrinol.* 6:549-555) and humans (Chiodera and col. (1996) Effects of intravenously infused pituitary adenylate cyclase activating polypeptide on adenohypophyseal hormone secretion innormal men. *Clin. Neuroendocrinol.* 64:242-246) it does not produce this effect.

These findings suggest that, in mammals, the peptide effect on the GH secretion varies species to species (Anderson and col. (2004) Growth Hormone Secretion: Molecular and Cellular Mechanisms and In Vivo Approaches. *Society for Experim. Biol. and Med.* 229:291-302).

Until now, no in vivo studies exist in fish that show the PACAP function in the GH regulation or the use of this peptide in the appetite stimulation in aquatic organisms. In crustaceans, so far, there is no evidence of the existence of this peptide and the cascade of signals that regulate the growth in these organisms is not known.

The PACAP stimulates the prolactin liberation by the pituitary cells in mammals (Ortmann and col. (1999) Interactions of ovarian steroids with pituitary adenylate cyclase-activating polypeptide and GnRH in anterior pituitary cells. *Eur. J. Endocrinol.* 140:207-214). It promotes melanotropin α-melanocyte-stimulating hormone (MSH) liberation by the melanotrophic cells of the pituitary. (Vaudry and col. (2000) Pituitary adenylate cyclase-activating polypeptide and its receptors: from structure to functions. *Pharmacol. Rev.s* 52:269-364).

In fish there are no studies, in vivo, that show the activity of this peptide in the prolactin liberation. Also there are no findings about its effect in the development of the fish color.

In mammals, the PACAP immune system function is very well characterized and there are several patents that describe their use in humans as an immunological response modulator. Until now there are no antecedents in the literature that explains the PACAP immune system function in aquatic organisms.

The PACAP gene has been cloned from several vertebrate species and the one protocordade (tunicate). In fish has been isolated in some species of salmon and catfish (Sherwood and col. (2000) The Origin and Function of the Pituitary Adenylate Cyclase-Activating polypeptide (PACAP)/Glucagon Superfamily *Endocrine Reviews* 21(6):619-670, golfish (Leung y col. (1999) Molecular cloning and tissue distribution of in pituitary adenylate cyclase-activating polypeptide (PACAP) the goldfish. *Rec. Progr. Mol. Comp. Endocrinol.* 338-388), zebrafish (Fradinger and Sherwood (2000) Characterization of the gene encoding both growth hormone-releasing hormone (GRF) and pituitary adenylate cyclase-activating polypeptide. *Mol. and Cell. Endocrinol.* 165:211-219), trucha (Krueckl and Sherwood. (2001) and trout (Krueckl and Sherwood. (2001) Developmental expression, alternative splicing and gene copy number for the pituitary adenylate cyclase-activating polypeptide (PACAP) and growth hormone-releasing hormone (GRF) gene in rainbow trout. *Molec. and Cell. Endocrinol.* 182:99-108). The U.S. Pat. No. 5,695,954 protects the isolation and purification of the genes nucleotide sequences that codify fish GHRH-PACAP polypeptide, as well as, vectors and host that express these sequences with the objective of being used to increase the growth in fish via transgenesis, introducing the mentioned genetic constructions in fertilized fish eggs. It also protected a method to detect transgenic fish that contain these sequences.

In this patent are reported specifically the gene sequences that codify for GHRH-PACAP polypeptide of the *Oncorhynchus Nerka, Clarias macrocephalus* and *Acispenser transmontanus* species.

In the present invention were used different variants of the PACAP aminoacid sequence, with N-terminal modifications, obtained in our laboratory for *Clarias gariepinus* and *Oreochromis niloticus* species. These variants were used in aquatic organisms as a growth stimulator non transgenically, by their administration, e.g., by immersion bath expressed in the *E. coli* and *P. pastoris* supernatant culture, without previous purification of them. Unexpectedly, we found that these variants are able, in these conditions, to promote a significant increase of the immunological activity in these organisms and to elevate the prolactin concentration in serum. These peptide properties had not been described for aquatic organisms.

Some authors have reported a growth stimulator effect in fish by the recombinant growth hormone administration by immersion bath. Nevertheless, the direct use of the growth hormone is subject to many regulatory requirements, as is the use of the transgenic fish that express the growth hormone or a growth hormone liberating factor.

In the present invention a non transgenic methodology is described to increase the growth and to improve the immune system of aquatic organisms, including invertebrates.

Nowadays, aquatic organisms are an important source of proteins, but the natural environment is fully exploited. For this reason, to increase the production it is necessary to culture these aquatic species (Pullin y col.; Conference Proceeding 7, 432 p. International Center for living Aquatic Resources Management. Manila, Philippines. 1982, ISSN 0115-4389).

To increase the efficiency of the aquatic culture, through the growth stimulation, increase of the organism survival and improvement of the quality of the larvaeis as an important problem to resolve in the aquaculture.

SUMMARY OF THE INVENTION

The present invention gives a solution for the problem mentioned above providing variants of Pituitary Adenylate Cyclase-Activating Polypeptide with the amino acids sequences identified as SEQ ID No 12, 13 and 14. They increase the rate of growth of the aquatic organisms, including invertebrate organisms, in a period of short time, which is very important for the aquaculture. In addition, these peptides increase the survival of fish larvae and crustaceans of commercial interest when are applied by immersion bath or as feed additive. They stimulate the immune activity in these organisms, as well as the appetite, the development of the fish colors and the prolactin liberation.

In a preferred embodiment of the present invention, the PACAP variants are applied to fish or crustaceans by periodic injections with intervals of 3 days to a concentration of 0.1 µg/g of animal weight, by immersion baths every 4 days in fresh water or sea water to a peptide concentration between of 100 to 200 µg/per liter of water and as feed additive to a concentration of 5 mg/Kg of formulated feed. It produces a significant increase of growth and a superior immune activity.

The PACAP variants offer advantages because of its small size (5 KDa), which permits good absorption through the skin and mucous of the organisms when it is applied by immersion bath. Administration provides advantages for the aquaculture and with a low index of contamination. In addition the PACAP signals transduction mechanism begins with the adenyl cyclase activation, not through the activation of a hormone, which is why its use displays better public perception and less regulatory requirements.

Other advantages of the PACAP variants are its capacity to stimulate the innate and adaptive immune activity in fish and to increase the resistance to pathogenic agents' infections.

In a materialization of the present invention, the PACAP variants are provided to aquatic organisms, such as, the tilapia *Oreochromis* sp, the catfish *Clarias* sp, the salmon *Salmon* sp. and the shrimps *Penaeus* sp.

In another preferred embodiment of the present invention, the variants of the PACAP are provided to the fish or crustaceans to prevent or to treat infections by pathogenic agents.

A materialization of the present invention describes a composition preparation to treat fish or crustaceans in culture to stimulate its growth and to increase its resistance against diseases, as well as for preventive or therapeutic treatment of an infection by pathogenic agents, all this with the objective to improve the productivity.

DETAILED DESCRIPTION OF PARTICULAR EMBODIMENTS/EXAMPLES

Example 1

Construction of the Expression Vectors Containing the Coding Sequences of PACAP for its Intracellular Expression in *E. coli* and its Extracellular Production in the Supernatant Culture of *P. pastoris*

The *Clarias gariepinus* PACAP gene was isolated by Polymerase Chain Reaction using the GHRH-PACAP cDNA as a template previously cloned into a T vector. We used the specific oligonucleotides corresponding to the sequences SEQ ID No 1 and SEQ ID No 2 to obtain the GHRH-PACAP complete sequence included signal peptide sequence, and specific oligonucleotides SEQ ID No 3 and SEQ ID No 4 to amplify only the PACAP gene with the restriction site necessary for its cloned in the *E. coli* expression vector.

The tilapia PACAP gene was isolated similarly as described above using the specific oligonucleotides SEQ ID No 3 and SEQ ID No 4. The present invention constitutes the first report of the isolation of this gene in tilapia.

Figure 1:
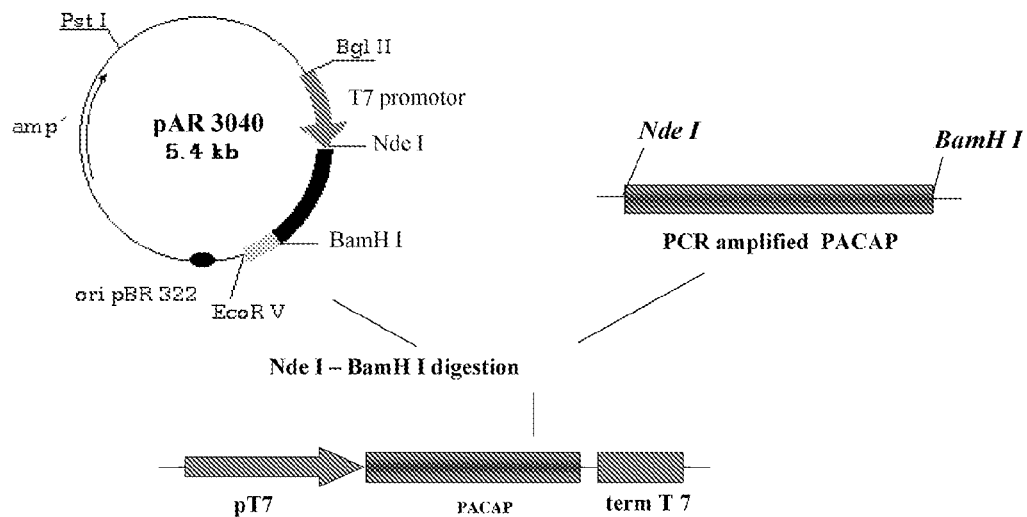
FIG. 1. The PACAP cloning strategy in the bacteria expression vector (FIG. 1A) and in the yeast expression vector (FIG. 1B).

The PACAP codifying sequence was cloned in the *E. coli* expression vector pAR 3040 using the restriction sites NdeI and BamHI (FIG. 1A). We selected one to the recombinant plasmid to transform the *E. coli* BL21D3 bacteria and to induce the PACAP expression under the regulation of the T7 promoter, using as inductor 0.5 mM IPTG.

The gene expression was carried out to 28° C. during 5 hours. The expression of the recombinant PACAP and its integrity were corroborated by Mass Spectrometry.

Figure 1B:
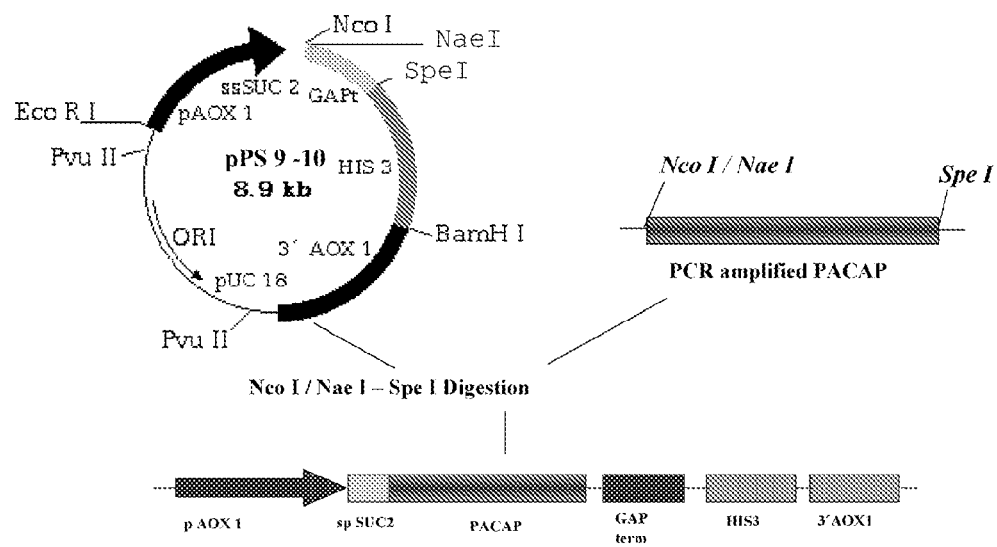

To express PACAP in *P. pastoris* we used the yeast expression vector pPS9 and pPS10. We used the specific oligonucleotides SEQ ID No 7 and SEQ ID No 6 for pPS9 gene cloning and the oligonucleotides SEQ ID No 5 and SEQ ID No 6 for pPS10 cloning. For pPS7 cloning we used the restriction sites NcoI and SpeI. This cloning approach adds to the interest protein a meteonyne and a glycine in the N-terminal for pPS10 cloning we used the restriction sites NaeI and SpeI, this cloning strategy does not add amino acids to the interest protein (FIG. 1B).

Prior to the transformation, the plasmids were linearized with the enzyme Sph I. The *Pichia pastoris* MP36 strain was transformed by electroporation with the recombinant expression vector. This strain is an auxotrophic mutant his3 which acquired a His$^+$ phenotype after transformation.

The transformants, identified by Dot Blot, were also analyzed by Southern blot to determinate in which ones the integration occurred by the replacement of the gene AOX1 of *P. pastoris* for the expression cassette of the recombinant plasmid. This integration event produces a Mut$^s$ (low levels of methanol utilization) and His$^+$ phenotypes. The genetic replacement of AOX1 occurs by recombination between the promoter regions AOX1 and 3'AOX1 in the vector and genome. As a result of the recombination, a deletion occurs in the coding region for AOX1. The recombinant strains with a Mut$^s$ phenotype support the alcohol oxidase production in the AOX2 gene and they have a low growth rate in methanol.

The genes encoding for the polypeptides of interest and tilapia growth hormone are under the regulation of the AOX1 promoter, inducible by methanol, and they have a signal peptide. *Pichia pastoris* secrete low levels of self proteins and its culture medium does not need proteins as supplements. Therefore, it can be expected that a secreted heterologous protein will be a high percent of the total proteins in the medium (more than 80%) (Tschopp y col.; Bio/Technology 1987, 5: 1305-1308; Barr et al.; Pharm. Eng. 1992, 12: 48-51). The production of the recombinant proteins explained in this invention was done in bioreactors of 5 L with the addition of methanol to the culture.

Example 2

Growth Stimulation Experiment in Juvenile *Clarias gariepinus*, Determination of the Hepatosomatic Index and Fish Muscle Dry Weight We used 18 catfish of the *Clarias gariepinus* species, without sex distinction, of approximately the same age and with average body weight of 30 to 40 grams.

Figure 2:
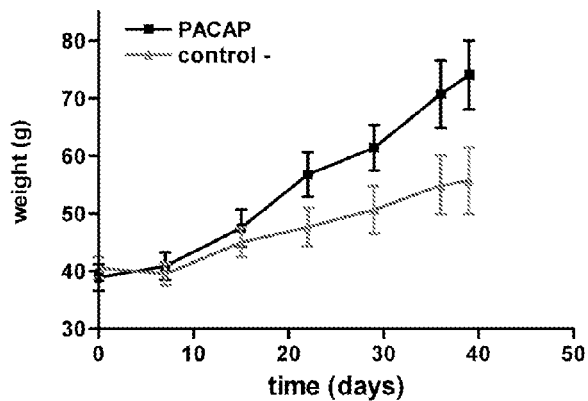
FIG. 2. Growth stimulation experiment in juvenile *Clarias gariepinus* by the intraperitoneal injection of the recombinant PACAP, purified by affinity chromatography, to the dose of 0.1 µg/g of animal weight. The graph represents the average of the corporal weight of the PACAP treated group compared with the control group.

Two experimental groups were formed having nine individuals in each. The groups were acclimated in separated tanks with stable water recirculation, to a temperature of 28° C. and with the photoperiod of 14 hours light and 10 hours dark. The animals were fed 2 times per day, with equivalent rations to 5% of the total corporal weight in each tank. The animals were identified before the experiment. A group was treated with semi-purified PACAP (70% of purity) SEQ ID No. 13, whereas the other one, used as a control group, was treated with *E. coli* proteins contained in PBS 1× (*E. coli* proteins were obtained by the same purification procedure of the interest peptide, with the amount equivalent of the contaminants presents in the purified PACAP sample). The PACAP treated fish were intraperitoneal injected at the dose of 0.1 μg of the peptide by gram of the animal corporal weight, 2 times per week. The control group was injected similarly as described above. 22 days after the beginning of the experiment, the PACAP injected animals in the peritoneal cavity, showed a significant increase (p<0.05) of the corporal body weight compared to the negative controls (FIG. 2).

The hepatosomatic index and the muscle dry weight were determined to demonstrate that the increase in the fish corporal body weight it was not due to the increase of the organs size, or to the increase of the muscle water content.

Figure 3:
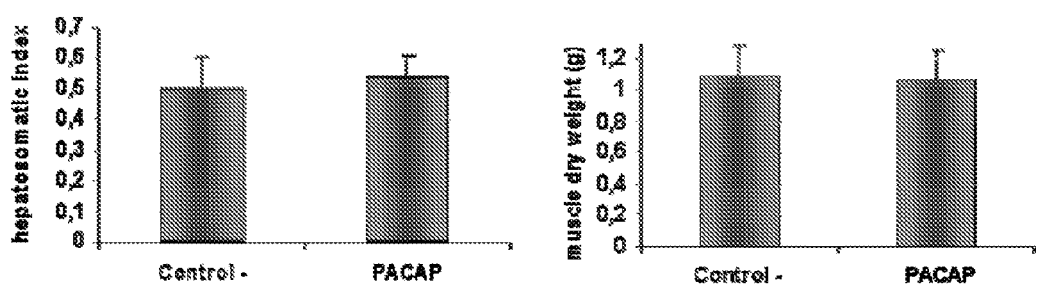
FIG. 3. Growth stimulation experiment in juvenile *Clarias gariepinus* by the intraperitoneal injection of the recombinant PACAP, purified by affinity chromatography, at the dose of 0.1 µg/g of animal weight. The graph represents the average of the hepatosomatic index and muscle dry weight of the PACAP treated group compared with the control group.

Significant differences between hepatosomatic index and muscle dry weight values of the experimental groups (FIG. 3) were not observed.

Similar results were obtained when the recombinant PACAP of the sequence SEQ ID No. 12 was applied.

Example 3

Experiment of Growth Stimulation, of the Resistance to Pathogenic Agents and of the Prolactin Liberation, in Tilapia Larvae by Immersion Baths with the *E. coli* Rupture Supernatants Containing the Recombinant PACAP We made an experiment to evaluate the function of the *Clarias gariepinus* recombinant PACAP present in the *E. coli* rupture supernatant in the tilapia larvae growth.

Figure 4A:
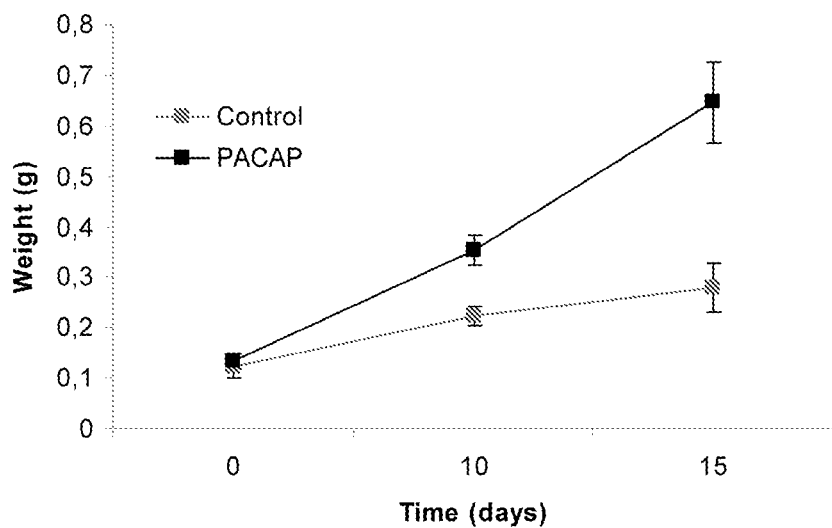
FIG. 4. Growth stimulation experiment in tilapia larvae by immersion in *E. coli* rupture supernatants containing the recombinant PACAP at the dose of 100 µg/liter of water. Graphic 4A and 4B represents the average body weight and length of treated-groups compared to negative controls.
Figure 4B:
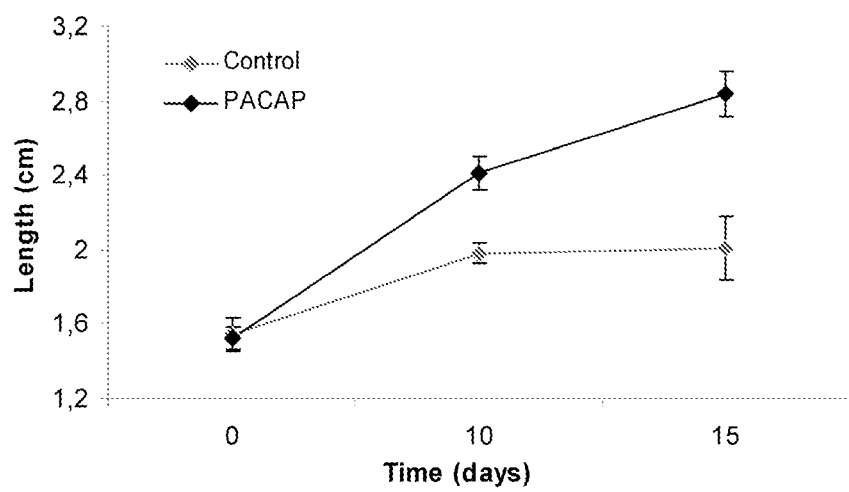
Figure 5:
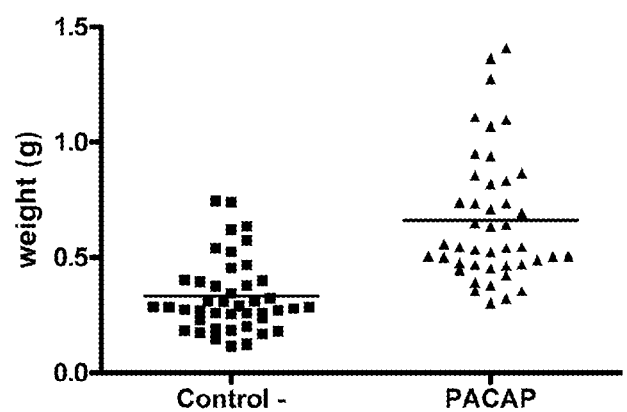
FIG. 5. Growth stimulation experiment in tilapia larvae by immersion in *E. coli* rupture supernatants containing the recombinant PACAP at the dose of 100 μg/liter of water. Graphic represents the average body weight of treated-groups compared to negative controls, 22 days after the beginning of the treatments.

Two experimental groups were formed having 60 individuals in each. One group was treated with the PACAP neuropeptide (SEQ ID No. 13) and the other one was used as a control group. The larvae groups were acclimated in separated tanks with stable water recirculation, to a temperature of 28° C. and with the photoperiod of 14 hours light and 10 hours dark and the animals were fed with the obtained amount from the following equation: Amount of food=# of animals×average body weight (g)×40%/100. The treatments consisted of immersion baths in 2 L of water, three times a week for 60 min during 20 days, the dose was 200 μg of target protein/liter of water. 10 days from the beginning of the experiment the PACAP treated group showed a significant corporal weight and length increase compared with the control group ($p<0.01$). 15 days from initiation the experiment the difference between the groups was highly significant ($p<0.001$) (Table 1 and FIGS. 4A and 4B). 20 days from the beginning of the immersion baths the differences between the PACAP treated group and the control group were statistically significant ($p<0.001$) (FIG. 5).

TABLE 1

Average in the body weight and length of the tilapia larvae, 10 days and 15 days of the beginning of the experiment.

| | Body weight (g) | | Length (cm) | |
|---|---|---|---|---|
| Treatment | 10 days | 15 days | 10 days | 15 days |
| PACAP | 0.3536 ± 0.0879 | 0.6458 ± 0.2399 | 2.41 ± 0.2726 | 2.84 ± 0.3627 |
| Control | 0.2221 ± 0.0565 | 0.2785 ± 0.1438 | 1.98 ± 0.1687 | 2.01 ± 0.5174 |

Mass and length are shown as mean ± S.D

Figure 6:
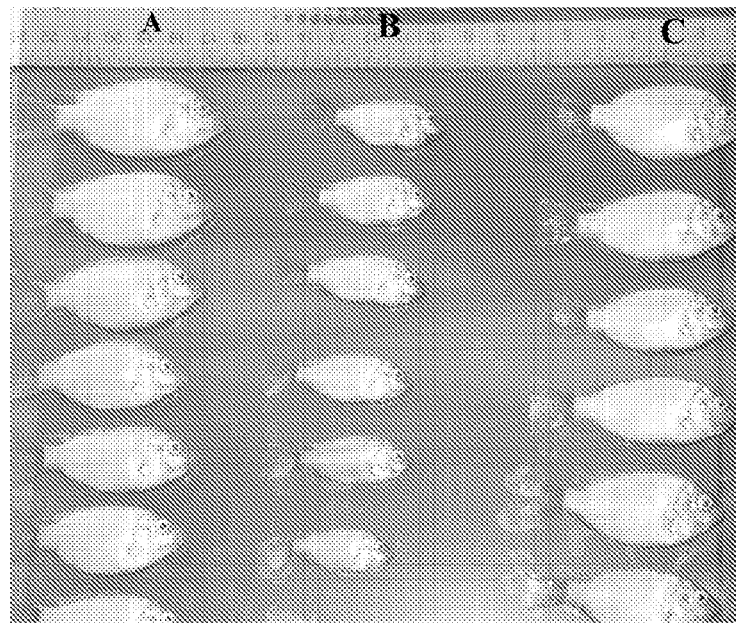
FIG. 6. Growth stimulation experiment in tilapia larvae by immersion in *E. coli* rupture supernatants containing the recombinant PACAP at the dose of 100 μg/liter of water. The picture shows the difference in length 30 days after the last immersion bath, of the PACAP treated fish (A and C) with respect to the control group (B).
Figure 7:
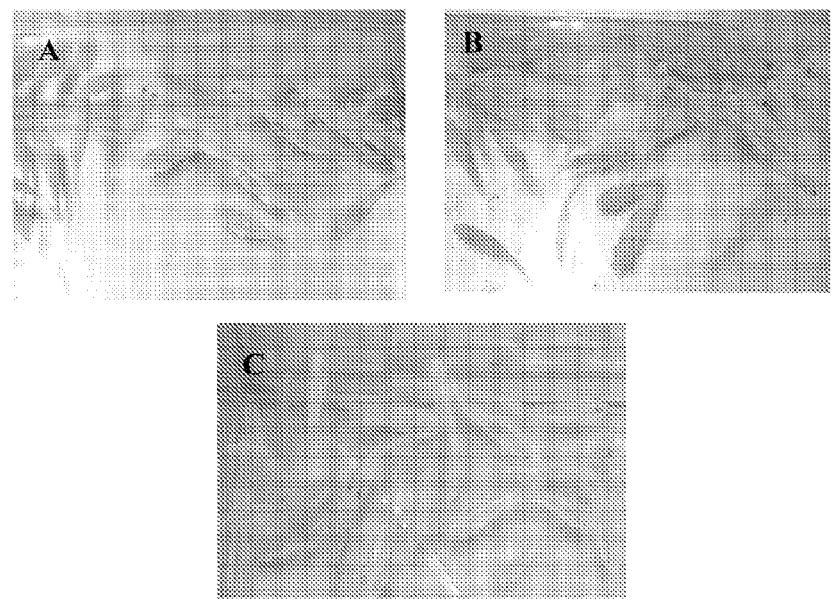
FIG. 7. Growth stimulation experiment in tilapia larvae by immersion in *E. coli* rupture supernatants containing the recombinant PACAP at the dose of 100 μg/liter of water. The picture shows the earlier development of the fish colors in the PACAP treated fish (A and B) respect to the control group (C).

It was observed that the effect of PACAP in the growth stayed in the time, because 30 days after the last immersion bath the differences in the corporal weight and the length of the experimental groups animals were very significant ($p<0.01$) (FIG. 6). In addition, it was observed that the PACAP treated fish showed the skin coloration in an early developmental stage compared with negative control (FIG. 7).

In this experiment we also studied the presence of the cutaneous protozoa *Trichodina* sp, 10 animals were selected at random of each experimental group and the invasion intensity by this pathogenic agent was determined. The values of invasion intensity were determined according to the equation:

$$(I: \text{\# total fish parasites}) I = \Sigma N/n - F_0 y$$

$$E = n - F_0 \times 100/n$$

I: (average invasion intensity) E: (# parasite fish from the total)
ΣN: (total of found parasites) $F_0$: (number of non parasite fish) n: (number of analyzed fish)

The PACAP treated fish showed an invasion intensity (average of I=2.20) by the protozoa *Trichodinas* sp significantly inferior ($p<0.01$) with respect to the control group (average of I=5.56).

The fish were treated by immersion bath 45 days from the beginning of the experiment in the same conditions previously described and 24 hours after the treatment the blood was extracted from 10 animals per group to measure prolactin in the serum by Western blot and ELISA. A polyclonal antibody anti tilapia prolactin was used for these assays. We observed statistical significant differences between PACAP treated group compared with control group $p<0.01$ (Table 2). These are very attractive results in the commercial aquatic organisms, as it is the case of the salmons, which have a life cycle in fresh water and sea water and in which the prolactin performs an important function in the osmoregulation.

TABLE 2

Prolactin concentration (ng/mL) in the tilapia serum 45 days from the begining of the experiment.

| Concentration of prolactin | PACAP TREATED GROUP | GROUP PLACEBO |
|---|---|---|
| ng/mL | 36.860 ± 2.695* | 15.745 ± 1.362 |

The concentration is shown as means ± S.D
*indicates a significant difference P < 0.01

Example 4

Experiment to Evaluate the Effect of Recombinant PACAP on the Juvenile Tilapia *Orechromis niloticus* Appetite Until now, the biological effects of the PACAP in the appetite, of fish have not been studied. In the submammalian vertebrate organisms the activity of this peptides in the appetite has been little characterized (Jensen, 2001, Regulatory peptides and control of food intake in non-mammalian vertebrates. *Comp. Biochem. And Phisiol. Part A* 128:471-479).

To analyze the effect of the PACAP in the fish appetite, we used tilapia of the *Oreochromis niloticus* species, without sex distinction and approximately the same average body weight. Three experimental groups were formed having 3 individuals in each and 3 replicates per group. The groups were acclimated in separated tanks with stable water recirculation, to a temperature of 28° C. and with the photoperiod of 14 hours light and 10 hours dark.

A group was treated with semi-purified PACAP (87% of purity) SEQ ID No. 13 by intraperitoneal injection of 0.5 μg/g of the animals body weight. The second group was treated with the GHRP-6 (Lipotec, S.A, Spain) by the same administration via at the dose of 0.1 μg of the peptide by gram of the animal corporal weight. The control group was treated with *E. coli* proteins contained in PBS 1× (*E. coli* proteins were obtained by the same purification procedure of the interest peptide, with the amount equivalent of the contaminants presents in the purified PACAP sample).

After the treatments, the same amount of food was added to the three experimental groups, collecting the non ingested food in 6 hour and adding food again. The appetite was measured again, 22 hours from the beginning of the experiment.

The food not ingested in each tank was dried in the stove (100° C., during 24 h) and was weighed in an analytical balance. The ingested food was calculated determining the difference between the food added to the tanks (10 grams, with a 20% of humidity) and the food not ingested by the fish.

Figure 8:
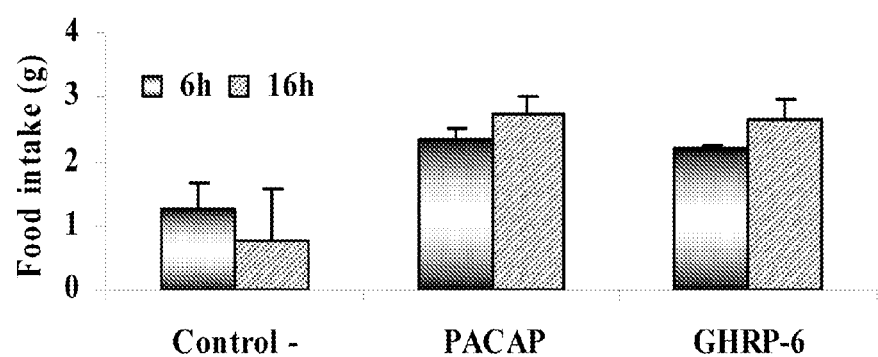
FIG. 8. Evaluation of the recombinant PACAP, purified by affinity chromatography, in the tilapia *Orechromis niloticus* appetite, at the dose of 0.5 μg/g of animal weight. The picture shows the average of food ingested by the fish in 6 hours and 22 hours of the beginning of the treatments.

The PACAP and GHRP-6 treated tilapia showed a significant appetite increase (p<0.05) compared with control group (FIG. 8).

Example 5

Evaluation of the Recombinant PACAP in the Catfish *Clarias gariepinus* Immune System Juvenile *Clarias gariepinus* were employed. Two groups were defined, with 10 individuals in each group. The groups were acclimated in separated tanks with stable water recirculation, to a temperature of 28° C. and with the photoperiod of 14 hours light and 10 hours dark. The animals were fed 2 times per day, with equivalent rations to 5% of the total corporal weight in each tank. The animals were identified before the experiment. The PACAP (SEQ ID No. 13) treated fish were intraperitoneal injected at the dose of 0.1 µg of the peptide by gram of the animal corporal weight, 2 times per week.

Twenty days from the initiation of the experiment the fish blood was extracted to measure the lysozyme and lectin levels in serum. The lysozyme activity in serum was measured using a method based on the ability of lysozyme to lyse the bacterium *Micrococcus lysodeikticus*. In a 96-well microtray, 100 µL of samples in four twofold serial dilutions in phosphate buffer (0.05 M, pH 6.2) were mixed with 100 µL of a 3 mg/ml suspension of *Micrococcus lysodeikticus* (Sigma). The microtray was incubated at 22° C. and the O.D. was read at 450 nm at 0, 2, 3, 5, 10, 15, 25, 35 and 45 min. For a positive control, fish serum was replaced by hen egg white lysozyme (serial dilutions starting at 8 µg/mL) and for a negative control, buffer replaced fish serum. A unit of lysozyme activity was defined as the amount of larval homogenates causing a decrease in the O.D. reading of 0.001 $min^{-1}$. We observed statistical significant differences (p<0.01) between PACAP treated groups compared with control group (Table 3).

TABLE 3

Lysozyme concentration (µg/mL) in the fish serum 20 days after the beginning of the experiment.

| LYSOZYME CONCENTRATION | PACAP TREATED GROUP | CONTROL GROUP |
|---|---|---|
| µg/mL | 21.765 ± 5.438* | 7.828 ± 8.393 |

The concentration is shown as means ± S.D
*indicates a significant difference P < 0.01

In order to determine the presence of lectin in sanguineous serum, we made a haemagglutination assay. Serial twofold dilutions of the serum were performed using PBS pH 7.2 in U-bottom shaped (96 wells, Greiner, Microlon) microtitre wells to which an equal volume of freshly prepared 2% erythrocyte suspension (rabbit in PBS) was added. Wells were incubated for 1 h at room temperature and the titer was read visually and being equal to the dilution in the last well to show agglutination (as manifested by an evenly distributed layer of cells over the whole well bottom). The haemagglutinin activity of samples was examined and for each titer value was obtained. The activity was expressed as titer, i.e. the reciprocal of the highest dilution showing complete agglutination.

The PACAP treated fish showed a significant increase of the lectin levels in serum compared with the control group (p<0.05) (Table 4).

TABLE 4

Titer of haemagglutinin activity (the reciprocal of the highest dilution showing complete agglutination) in the fish serum at 45 days from the beginning of the experiment.

| | PACAP TREATED GROUP | CONTROL GROUP |
|---|---|---|
| TITER | 4* | 1 |

Student test.
*indicates a significant difference P < 0.05

Example 6

Experiment of Growth Stimulation in Tilapia Larvae by Immersion with *P. pastoris* Culture Supernatants Containing Recombinant PACAP We made an experiment to evaluate the function of the *Clarias gariepinus* PACAP (SEQ ID No 14) containing in *P. pastoris* culture supernatants in the growth of the tilapia larvae.

Three experimental groups were formed having 50 larvae in each. One group was treated with recombinant PACAP (SEQ ID No. 14) containing in *P. pastoris* culture supernatants. The second group was treated with the recombinant tilapia growth hormone (GH) containing in *P. pastoris* culture supernatants. The control group was treated with non-transformed *P. pastoris* culture supernatant. The larvae were fed twice to the day, with the obtained amount from the following equation: Amount of food=# of animals×average body weight (g)×40%/100. The treatment was done by immersion in the volume of 30 L, three times a week for 90 min. The dose was 100 µg of target protein/liter of water.

5 weeks (35 days) from the beginning of the experiment the PACAP treated group showed a significant corporal weight increase compared with the control group (p<0.01). The growth hormone treated group showed a significant increase of the corporal weight compared with the control group (p<0.05) (Table 5).

TABLE 5

Tilapia larvae weight in grams.

| TIME (DAYS) | PACAP TREATED GROUP | GH TREATED GROUP | CONTROL GROUP |
|---|---|---|---|
| 0 | 0.1013 ± 0.0625 | 0.1140 ± 0.0457 | 0.1040 ± 0.0535 |
| 35 | 0.9870 ± 0.0525 | 0.7875 ± 0.0422 | 0.4566 ± 0.0363 |

Mass is shown as mean ± S.D

Example 7

Experiment of Growth Stimulation and Improvement in Larvae Quality in the Shrimp *Litopenaeus schmitti* Treated with *Pichia pastoris* Culture Supernatants Containing the Recombinant PACAP We used the shrimp's larvae of the *Litopenaeus schmitti* species. Two experimental groups were formed having 100 larvae in each. One group was treated with recombinant PACAP (SEQ ID No. 14) containing in *P. pastoris* culture supernatants and the other used as a control group was treated with non-transformed *P. pastoris* culture supernatant.

The larvae were cultivated in fiber glass tanks with the capacity of 100 L. The feeding was based on dyatomeas (*Chaetoceros gracilis*), the flagellated algae (*Tetraselmis suecica*) and Artemia nauplius (Aquatic Eco-Systems Inc.).

The abiotic growth factors were the following ones:
illumination (24:00 L/D)
Stable aeration.
Salinity of 34 ppm.
Dissolved oxygen 5.2±0.5 (in the larvae cycle).
Recirculation alter $PZ_{III}$ of the 80%

Four immersion baths were applied to the experimental groups, one every three days of 1 hour of duration.

The PACAP treated group showed a significant corporal weight increase compared with the control group (p<0.01) (Table 6).

TABLE 6

Shrimp larvae weight in milligrams.

| TIME (DAYS) | PACAP TREATED GROUP | CONTROL GROUP |
|---|---|---|
| 0 | 0.3045 ± 0.0425 | 0.3273 ± 0.0420 |
| 30 | 12.5034 ± 0.0455 | 6.5325 ± 0.0438 |

Mass is shown as mean ± S.D

The PACAP treated group had a higher homogeneity and better quality of the larvae (more branquial ramifications and rostral modifications) which is very important in shrimp farming. The difference in the PL9 stage survival was greater than 40% in PACAP treated group.

Example 8

Growth Stimulation in Juvenile *Clarias gariepinus* by Including Recombinant PACAP in the Fish Diet Formulation The *Pichia pastoris* culture supernatant containing the recombinant PACAP (SEQ ID No. 14) was concentrated and formulated in the nutritional fish diet to a concentration of approximately 5 mg/Kg of feed.

Two experimental groups were formed having 100 larvae in each with an average body weight of 0.1 g. One group was treated with recombinant PACAP (SEQ ID No. 14) containing in *P. pastoris* culture supernatants and the other used as a control group was treated with non-transformed *P. pastoris* culture supernatant. The experiment was carried out during 30 days.

The recombinant PACAP (SEQ ID No. 14) included in the diet at the dose of 5 mg/Kg of feed increased growth in 30% compared with control group with highly significant statistical differences (p<0.01).

The invention claimed is:

1. A method to increase the productivity of crustaceans in culture,
said method comprising feeding or administering the neuropeptide pituitary adenylate cyclase activating peptide (PACAP), having the sequence selected from the group consisting of SEQ ID NO: 12, SEQ ID NO: 13, and SEQ ID NO: 14, to said crustaceans in culture in an amount effective to stimulate growth or to increase resistance against disease or both.

2. The method according to claim 1, wherein the PACAP neuropeptide is used to increase prolactin secretion and to improve osmorregulation.

3. The method according to claim 1, wherein the PACAP neuropeptide is used to stimulate the appetite in the crustaceans.

4. The method according to claim 1, wherein the PACAP neuropeptide is used to improve the development of coloration in the crustaceans.

5. The method according to claim 1, wherein the PACAP neuropeptide is obtained by chemical synthesis.

6. The method according to claim 1, wherein the PACAP neuropeptide is obtained by recombinant technology.

7. The method according to claim 6, wherein the PACAP neuropeptide is purified.

8. The method according to claim 1, wherein the PACAP neuropeptide is applied to said crustaceans by periodic injections every 3 days at the concentration of 0.1 µg/g of animal weight.

9. The method according to claim 1, wherein the PACAP neuropeptide is supplied to said crustaceans by immersion baths at intervals of 1 to 4 days in fresh water or sea water, in a concentration between 100 to 200 µg of the PACAP per liter of water.

10. The method according to claim 1, wherein the PACAP neuropeptide is supplied to said crustaceans as a formulated feed in a concentration of 5 mg of the PACAP/Kg of feed.

11. The method according to claim 1, wherein the PACAP neuropeptide is supplied to *Penaeus* sp. shrimp.

12. A method of stimulating growth in crustaceans in culture, said method comprising administering an effective amount of a pituitary adenylate cyclase activating peptide (PACAP) neuropeptide having the sequence selected from the group consisting of SEQ ID NO: 12, SEQ ID NO: 13, and SEQ ID NO: 14.

13. A method of increasing disease resistance in fish in culture, said method comprising directly administering to said fish an effective amount of a pituitary adenylate cyclase activating peptide (PACAP) neuropeptide produced in a supernatant of genetically transformed hosts without previous purification of said PACAP, said PACAP having the sequence selected from the group consisting of SEQ ID NO: 12, SEQ ID NO: 13, and SEQ ID NO: 14.

14. The method according to claim 13, wherein the supernatant is *E. coli* culture supernatant.

15. The method according to claim 13, wherein the supernatant is *P. pastoris* culture supernatant.

16. The method according to claim 13, wherein the PACAP neuropeptide is supplied to *Oreochromis* sp. tilapia.

17. The method according to claim 13, wherein the PACAP neuropeptide is supplied to *Clarias* sp. catfish.

18. The method according to claim 13, wherein the PACAP neuropeptide is supplied to *Salmon* sp. salmon.

19. The method according to claim 13, wherein said administration is selected from injection, immersion, or as a food additive.

20. A method of stimulating growth in fish in culture, said method comprising directly administering to said fish an effective amount of a pituitary adenylate cyclase activating peptide (PACAP) neuropeptide produced in a supernatant of genetically transformed hosts without previous purification of said PACAP, said PACAP having the sequence selected from the group consisting of SEQ ID NO: 12, SEQ ID NO: 13, and SEQ ID NO: 14.

21. The method according to claim 20, wherein said administration is selected from injection, immersion, or as a food additive.

* * * * *